United States Patent [19]
Grisoni et al.

[11] Patent Number: 5,756,127
[45] Date of Patent: May 26, 1998

[54] IMPLANTABLE BIORESORBABLE STRING OF CALCIUM SULFATE BEADS

[75] Inventors: Bernard F. Grisoni, Cordova, Tenn.; Steve Gitelis, Oakbrook, Ill.; Timothy L. Harrison, Memphis, Tenn.; Jack E. Parr, Bartlett, Tenn.; Ben R. Shappley, Germantown, Tenn.

[73] Assignee: Wright Medical Technology, Inc., Arlington, Tenn.

[21] Appl. No.: 736,715

[22] Filed: Oct. 29, 1996

[51] Int. Cl.$^6$ .............................. A61K 9/18; A61K 47/02
[52] U.S. Cl. .................... 424/489; 424/426; 424/9.4; 424/696; 514/953; 514/769; 604/891.1
[58] Field of Search .................... 424/426, 489, 424/696; 514/953, 769; 428/402; 604/891.1

[56] References Cited

U.S. PATENT DOCUMENTS

| | | |
|---|---|---|
| 4,610,692 | 9/1986 | Eitenmuller et al. |
| 4,619,655 | 10/1986 | Hanker et al. |
| 4,853,225 | 8/1989 | Wahlig et al. |
| 5,147,403 | 9/1992 | Gitelis. |
| 5,258,291 | 11/1993 | Inoue et al. |
| 5,268,178 | 12/1993 | Calhoun et al. |
| 5,281,419 | 1/1994 | Tuan et al. |
| 5,334,626 | 8/1994 | Lin. |
| 5,641,514 | 6/1997 | Cho. |

*Primary Examiner*—Edward J. Webman
*Attorney, Agent, or Firm*—Walker, McKenzie & Walker, P.C.

[57] ABSTRACT

A bioresorbable string of implantable beads in which the beads consist essentially of calcium sulfate and a quantity of a drug suitable for treating tissue disorders, and in which both the beads and the line that joins the beads together are bioresorbable.

6 Claims, 4 Drawing Sheets

IMPLANTABLE BIORESORBABLE STRING OF CALCIUM SULFATE BEADS

BACKGROUND OF THE INVENTION

1. Field of the Invention

The present invention relates, in general, to means for and methods of treating orthopedic tissue disorders and, more specifically, to implantable bioresorbable beads for treating orthopedic tissue disorders, and to a mold for and method of manufacturing beads for treating orthopedic tissue disorders.

2. Information Disclosure Statement

Osteomyelitis is an example of tissue disorder treated by implantation of local drug delivery devices. Surgeons currently implant bone cement beads containing antibiotics near the infected site to locally release drugs and advantageously treat infection. Such bone cement beads are not bioresorbable and have to be subsequently explanted. A plurality of such bone cement beads are generally attached as a group to a steel wire to facilitate proper positioning and explanation.

Plaster of Paris (calcium sulfate hemihydrate) has been used to fill bone cavities, and is resorbed in vivo so that subsequent explanation is not necessary. It has been suggested that small antibiotic loaded plaster of Paris beads or pellets be used to fill bone cavities and simultaneously treat infection. Such antibiotic loaded plaster of Paris beads or pellets would also be resorbed in vivo so that subsequent explanation is not necessary.

A preliminary patentability search produced the following patents which appear to be relevant to the present invention:

Eitenmuller et al., U.S. Pat. No. 4,610,692, issued Sep. 9, 1986, discloses a sintered tricalcium phosphate implant for filling bone cavities and for fixing bone fragments. The implant includes a discretely-shaped porous body, at least one therapeutically-active ingredient impregnated into the porous body and distributed among the pores therein, and at least one coating of predetermined thickness of a biodegradable substance on at least a portion of the porous body so that the time of absorption of the therapeutically-active ingredient is controlled by the thickness of the biodegradable substance.

Hanker et al., U.S. Pat. No. 4,619,655, issued Oct. 28, 1986, discloses an animal implant comprising a scaffold material composed of plaster of Paris and a non-bioresorbable calcium material (such as calcium phosphate ceramic particles) bound with the plaster of Paris; a method of inserting such a composition in fluid or semisolid form into the appropriate body location of an animal (e.g., about a fracture locus); and a method of inserting a preform of such composition into the appropriate location of an animal (e.g., at the locus of a fracture).

Gitelis, U.S. Pat. No. 5,147,403, issued Sep. 15, 1992, discloses a method or technique for implanting a prosthesis comprising the steps of first preparing the surface of a bone to receive the prosthesis, then applying a calcium sulfate suspension in free flowing form to the prepared bone surface, and then seating the prosthesis to the coated bone surface.

Inoue et al., U.S. Pat. No. 5,258,291, issued Nov. 2, 1993, discloses a method for separating and recovering polymeric beads from an antibiotic fermentation broth, including the steps of suspending a mixture of the beads and any inherent mold from the fermentation in an aqueous solution having a specific gravity which is effective to cause the beads to form a discrete layer at or on the surface of the solution, separate and apart from the mold. The separate layer of the beads may then be physically removed from the liquid.

Calhoun et al., U.S. Pat. No. 5,268,178, issued Dec. 7, 1993, discloses a biodegradable implant comprised of at least one biodegradable material such as polylactic acid, and at least one antibiotic drug.

Tuan et al., U.S. Pat. No. 5,281,419, issued Jan. 25, 1994, discloses an antibiotic impregnated fracture fixation device and drug delivery polymer employing a homogenous mixture of thermally melted polylactic acid and at least one antibiotic or antibacterial agent.

Lin, U.S. Pat. No. 5,334,626, issued Aug. 2, 1994, discloses a bone cement composition having adjustable Theological properties, and produces a uniform radiological image. The cement comprises beads containing a polymerization initiator anyd may include additives such as antibiotics, bone growth factors, and other pharmacological or therapeutic agents.

Nothing in the known prior art discloses or suggests the present invention. More specifically, nothing in the known prior art discloses or suggests a bioresorbable string of implantable beads in which the beads contain a quantity of a drug suitable for treating tissue disorders, and in which both the beads and the line that joins the beads together are bioresorbable. Further, nothing in the prior art discloses or suggests a mold for molding a string of implantable beads used to treat orthopedic tissue disorders, the mold comprising a body member having a face surface, a cavity including a contour with a cross sectional area having a maximum width dimension, and a mouth in the face surface thereof communicating with the cavity thereof for allowing a quantity of a fluid mixture to be introduced into the cavity, the mouth having a minimum width dimension that is less than the maximum width dimension of the cross sectional area of the contour of the first cavity. In addition, nothing in the prior art discloses or suggests a method of manufacturing a string of implantable beads used to treat orthopedic tissue disorders, the method comprising the steps of providing a mold including a body member having a face surface; a first cavity including a contour with a cross sectional area having a maximum width dimension; a first mouth extending from the face surface to the first cavity for allowing a quantity of a fluid mixture to be introduced into the first cavity; the first mouth having a minimum width dimension that is less than the maximum width dimension of the cross sectional area of the contour of the first cavity; a second cavity including a contour with a cross sectional area having a maximum width dimension; and a second mouth extending from the face surface to the second cavity for allowing a fluid or semisolid mixture to be introduced into the second cavity; the second mouth having a minimum width dimension that is less than the maximum width dimension of the cross sectional area of the contour of the second cavity; stringing an elongated line between the first and second cavities; filling the first and second cavities of the body member of the mold with a fluid mixture by inserting a quantity of the fluid mixture through the first and second mouths into the first and second cavities, respectively, until the cavities and the mouths are filled with the fluid mixture; after the first and second cavities of the body member have been filled with the fluid mixture and after the line and been strung between the first and second cavities, allowing the fluid mixture to set; and then removing the set mixture from the first and second cavities by pulling the line away from the body member.

SUMMARY OF THE INVENTION

The present invention describes biocompatible bioresorbable beads containing drugs suitable for treating tissue disorders such as antibiotics (Tobramycin, Vancomycin, etc.) for bone infection treatment, antineoplastic substances for cancer treatment, analgesics for pain release, etc. The beads can be attached to a bioresorbable suture to facilitate handling and insertion. Calcium sulfate is an example of bioresorbable material which can be used for this application. It is biocompatible and has radiopaque properties. Beads made of calcium sulfate can be used as a bioresorbable bone void filler or bioresorbable X-ray markers. Calcium sulfate can also be mixed with a wide range of therapeutic agents to make implantable biological repair devices that release the therapeutic agent locally as the calcium sulfate dissolves after implantation.

One object of the present invention is to provide a bioresorbable string of implantable beads in which the beads contain a quantity of a drug suitable for treating tissue disorders, and in which both the beads and the line that joins the beads together are bioresorbable.

Another object of the present invention is to provide a mold for molding a string of implantable beads used to treat orthopedic tissue disorders, the mold comprising a body member having a face surface, a cavity including a contour with a cross sectional area having a maximum width dimension, and a mouth in the face surface thereof communicating with the first cavity thereof for allowing a quantity of a fluid mixture to be introduced into the cavity, the mouth having a minimum width dimension that is less than the maximum width dimension of the cross sectional area of the contour of the cavity.

Another object of the present invention is to provide a method of manufacturing a string of implantable beads used to treat orthopedic tissue disorders, the method comprising the steps of providing a mold including a body member having a face surface; a first cavity including a contour with a cross sectional area having a maximum width dimension; a first mouth extending from the face surface to the first cavity for allowing a quantity of the fluid mixture to be introduced into the first cavity; the first mouth having a minimum width dimension that is less than the maximum width dimension of the cross sectional area of the contour of the first cavity; a second cavity including a contour with a cross sectional area having a maximum width dimension; and a second mouth extending from the face surface to the second cavity for allowing a fluid or semisolid mixture to be introduced into the second cavity; the second mouth having a minimum width dimension that is less than the maximum width dimension of the cross sectional area of the contour of the second cavity; stringing an elongated line between the first and second cavities; filling the first and second cavities of the body member of the mold with a fluid mixture by inserting a quantity of the fluid mixture through the first and second mouths into the first and second cavities, respectively, until the cavities and the mouths are filled with the fluid mixture; after the first and second cavities of the body member have been filled with the fluid mixture and after the line and been strung between the first and second cavities, allowing the fluid mixture to set; and then removing the set mixture from the first and second cavities by pulling the line away from the body member.

BRIEF DESCRIPTION OF THE DRAWINGS

FIG. 11 is an enlarged sectional view of the first body member of the mold of FIG. 7, taken on a plane substantially transverse to the plane that FIG. 10 is taken on.

DESCRIPTION OF THE PREFERRED EMBODIMENTS

The preferred embodiments of the present invention includes a string of implantable beads for treating orthopedic tissue disorders, a mold for molding such a string of implantable beads, and a method of manufacturing such a string of implantable beads. Unless specifically limited, the word "beads" is used herein in a broad sense to mean any substantially solid body of various specific shapes and sizes, etc., capable of being implanted in a void V in a bone B which may have been caused by prior surgery, a bone tumor or cyst, trauma, etc.

Figure 1:
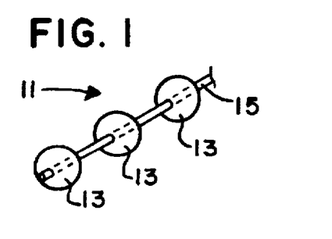
FIG. 1 is a perspective view of a first embodiment of a bioresorbable string of implantable beads of the present invention.
Figure 2:
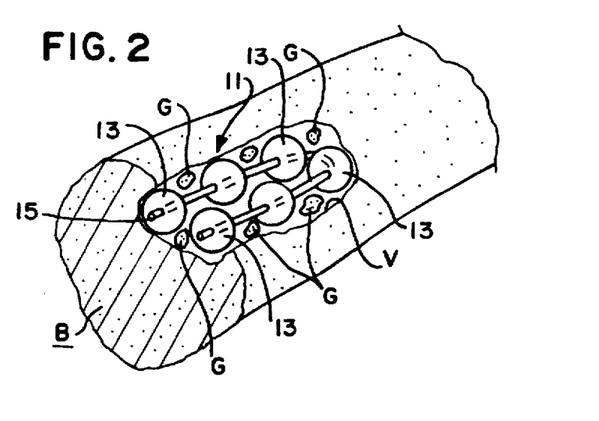
FIG. 2 is a perspective view of the bioresorbable string of implantable beads, shown implanted in a void in a bone.

A first preferred embodiment of a bioresorbable string of implantable beads of the present invention is shown in FIGS. 1 and 2, and identified by the number 11. The bioresorbable string 11 of implantable beads is used to treat orthopedic tissue disorders such as, for example, osteomyelitis.

The bioresorbable string 11 of implantable beads includes a plurality of bioresorbable beads 13. Each of the plurality of bioresorbable beads 13 contains a quantity of a drug or a combination of drugs suitable for treating tissue disorders such as, for example, a quantity of antibiotics (Tobramycin, Vancomycin, etc.) for bone infection treatment, a quantity of antineoplastic substances for cancer treatment, or a quantity of analgesics for pain release, etc. Each of the plurality of bioresorbable beads 13 is preferably manufactured out of a mixture of calcium sulfate and the desired quantity of drug or drugs. For example, each of the plurality of bioresorbable beads 13 can be manufactured out of a mixture of 69% medical grade calcium sulfate, 29% saline, and 2% Tobramycin. However, it will be understood that the ratio of the ingredient and the type of drug used, etc., can be varied. Calcium sulfate is a biocompatible, bioresorbable material which has radiopaque properties. Beads 13 made of calcium sulfate can be used as bioresorbable bone void filler or bioresorbable X-ray markers. Calcium sulfate can be mixed with a wide range of therapeutic agents to make implantable devices. The shape of each of the plurality of bioresorbable beads may be selected to provide an optimum rate of resorption and drug delivery. For, example, as clearly shown in FIGS. 1 and 2, each of the plurality of bioresorbable beads 13 of the first preferred embodiment of the bioresorbable string 11 of implantable beads is preferably substantially spherical in shape. The substantially spherical shape of the beads 13 will provide a certain rate of resorption and drug delivery as will now be apparent to those skilled in the art.

The bioresorbable string 11 of implantable beads includes a bioresorbable line 15 extending between and joining each of the plurality of bioresorbable beads 13 to facilitate handling and insertion. The bioresorbable line 15 preferably consists of a typical, off-the-shelf bioresorbable suture such as, for example, 2–0 coated Vicryl™ violet braided bioresorbable suture manufactured out of Polyglactin 910 by Ethicon, Inc. of Somerville, N.J.

The bioresorbable string 11 of implantable beads can be used by merely implanting a desired quantity of bioresorbable beads 13, joined together by a length of bioresorbable line 15, and containing a desired mixture of a therapeutic agent, into a void V in a bone B (see FIG. 2), or otherwise near an infected site to be treated. The therapeutic agent is locally released as the beads 13 dissolve after implantation. When implanted into a void V in a bone B, bone graft G or the like (e.g., actual bone or a bone substitute or bone inducing material) can be packed about the bioresorbable string 11 within the void V for promoting bone growth and fusion within the void V as will now be apparent to those skilled in the art.

Figure 3:
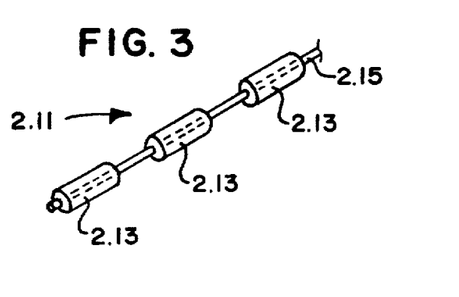
FIG. 3 is a perspective view of a second embodiment of a bioresorbable string of implantable beads of the present invention.

A second preferred embodiment of a bioresorbable string of implantable beads of the present invention is shown in FIG. 3, and identified by the number 2.11. The bioresorbable string 2.11 of implantable beads is preferably substantially identical to the bioresorbable string 11 of implantable beads and includes, in general, a plurality of bioresorbable beads 2.13 joined by a bioresorbable line 2.15. The difference between bioresorbable string 11 of implantable beads and the bioresorbable string 2.11 of implantable beads is the shape of the beads 13, 2.13. More specifically, the beads 2.13 of the bioresorbable string 2.11 of implantable beads are preferably substantially cylindrical in shape. The substantial cylindrical shape of the beads 2.13 of the bioresorbable string 2.11 of implantable beads will provide a certain rate of resorption and drug delivery that differs from the rate of resorption and drug delivery of the substantial spherical shape of the beads 13 of the bioresorbable string 11 of implantable beads as will now be apparent to those skilled in the art. Reference should be made to the above disclosure of the bioresorbable string 11 of implantable beads for a complete and thorough understanding of the construction and function of the bioresorbable string 2.11 of implantable beads.

Figure 4:
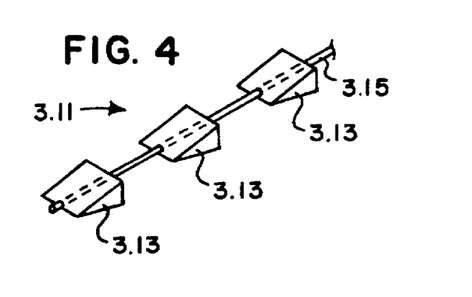
FIG. 4 is a perspective view of a third embodiment of a bioresorbable string of implantable beads of the present invention.

A third preferred embodiment of a bioresorbable string of implantable beads of the present invention is shown in FIG. 4, and identified by the number 3.11. The bioresorbable string 3.11 of implantable beads is preferably substantially identical to the bioresorbable string 11 of implantable beads and includes, in general, a plurality of bioresorbable beads 3.13 joined by a bioresorbable line 3.15. The difference between bioresorbable string 11 of implantable beads and the bioresorbable string 3.11 of implantable beads is the shape of the beads 13, 3.13. More specifically, the beads 3.13 of the bioresorbable string 2.11 of implantable beads are preferably substantially wedge shaped. The substantial wedge shape of the beads 3.13 of the bioresorbable string 3.11 of implantable beads will provide a certain rate of resorption and drug delivery that differs from the rate of resorption and drug delivery of the substantial spherical shape of the beads 13 of the bioresorbable string 11 of implantable beads and of the substantial cylindrical shape of the beads 2.13 of the bioresorbable string 2.11 of beads as will now be apparent to those skilled in the art. Reference should be made to the above disclosure of the bioresorbable string 11 of implantable beads for a complete and thorough understanding of the construction and function of the bioresorbable string 3.11 of implantable beads.

Figure 5:
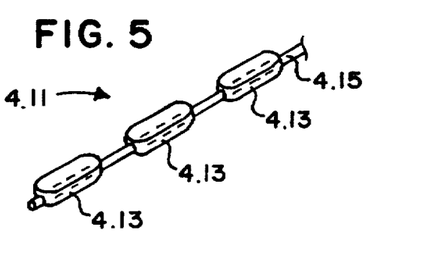
FIG. 5 is a perspective view of a fourth embodiment of a bioresorbable string of implantable beads of the present invention.

A fourth preferred embodiment of a bioresorbable string of implantable beads of the present invention is shown in FIG. 5, and identified by the number 4.11. The bioresorbable string 4.11 of implantable beads is preferably substantially identical to the bioresorbable string 11 of implantable beads and includes, in general, a plurality of bioresorbable beads 4.13 joined by a bioresorbable line 4.15. The difference between bioresorbable string 11 of implantable beads and the bioresorbable string 4.11 of implantable beads is the shape of the beads 13, 4.13. More specifically, the beads 4.13 of the bioresorbable string 4.11 of implantable beads are preferably substantially tablet shaped. The substantial tablet shape of the beads 4.13 of the bioresorbable string 4.11 of implantable beads will provide a certain rate of resorption and drug delivery that differs from the rate of resorption and drug delivery of the substantial spherical shape of the beads 13 of the bioresorbable string 11 of implantable beads, of the substantial cylindrical shape of the beads 2.13 of the bioresorbable string 2.11 of beads, and of the substantial wedge shape of the beads 3.13 of the bioresorbable string 3.11 of beads as will now be apparent to those skilled in the art. Reference should be made to the above disclosure of the bioresorbable string 11 of implantable beads for a complete and thorough understanding of the construction and function of the bioresorbable string 4.11 of implantable beads.

Figure 6:
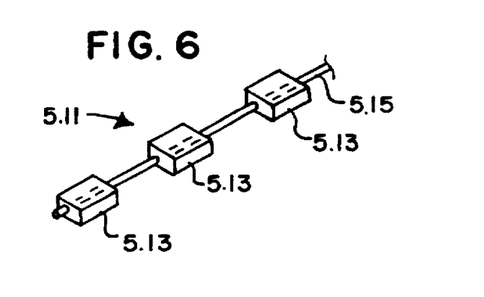
FIG. 6 is a perspective view of a fifth embodiment of a bioresorbable string of implantable beads of the present invention.

A fifth preferred embodiment of a bioresorbable string of implantable beads of the present invention is shown in FIG. 6, and identified by the number 5.11. The bioresorbable string 5.11 of implantable beads is preferably substantially identical to the bioresorbable string 11 of implantable beads and includes, in general, a plurality of bioresorbable beads 5.13 joined by a bioresorbable line 5.15. The difference between bioresorbable string 11 of implantable beads and the bioresorbable string 5.11 of implantable beads is the shape of the beads 13, 5.13. More specifically, the beads 5.13 of the bioresorbable string 5.11 of implantable beads are preferably substantially block shaped. The substantial block shape of the beads 5.13 of the bioresorbable string 5.11 of implantable beads will provide a certain rate of resorption and drug delivery that differs from the rate of resorption and drug delivery of the substantial spherical shape of the beads 13 of the bioresorbable string 11 of implantable beads, of the substantial cylindrical shape of the beads 2.13 of the bioresorbable string 2.11 of beads, of the substantial wedge shape of the beads 3.13 of the bioresorbable string 3.11 of beads, and of the substantial tablet shape of the beads 4.13 of the bioresorbable string 4.11 of beads as will now be apparent to those skilled in the art. Reference should be made to the above disclosure of the bioresorbable string 11 of implantable beads for a complete and thorough understanding of the construction and function of the bioresorbable string 5.11 of implantable beads.

A preferred embodiment of a mold of the present invention is shown in FIGS. 7–20, and identified by the numeral 21. The mold 21 is used for molding a string of implantable beads used to treat orthopedic tissue disorders. For illustrative purposes, the mold 21 will be described hereinbelow as used for molding a bioresorbable string 11 of implantable beads as disclosed hereinabove. However, it should be noted that the mold 21 can be used for molding beads of different shapes and sizes, and out of different and/or non-bioresorbable material such as beads molded from bone cement and joined together by metallic wire, etc.

The mold 21 includes a body member, hereinafter referred to as the first or normally lower body member 23, and preferably includes a second or normally upper body member 25 as shown generally in FIG. 7.

The first body member 23 has a face or normally upper surface 27.

The first body member 23 has a first cavity 29 including a contour with a cross sectional area having a maximum width dimension 31; a first mouth 33 in the face surface 27 thereof communicating with the first cavity 29 thereof for allowing a quantity of fluid mixture M to be introduced into the first cavity 29, the first mouth 33 having a minimum width dimension 35 that is less than the maximum width dimension 31 of the cross sectional area of the contour of the first cavity 29. The first body member 23 preferably has an enlarged counterbore-like depression 36 in the face surface 27 thereof about the first mouth 33 and communicating with the first cavity 29.

The first body member 23 preferably has a second cavity 37 including a contour with a cross sectional area having a maximum width dimension 39; and a second mouth 41 in the face surface 27 thereof communicating with the second cavity 37 thereof for allowing a quantity of the fluid mixture M to be introduced into the second cavity 37, the second mouth 41 having a minimum width dimension 43 that is less than the maximum width dimension 39 of the cross sectional area of the contour of the second cavity 37. The first body member 23 also preferably has an enlarged counterbore-like depression 44 in the face surface 27 thereof about the second mouth 41 and communicating with the first cavity 29.

At least a portion of the first body member 23 adjacent the first mouth 33 and the second mouth 41 is preferably movable. For example, the first body member 23 is preferably manufactured out of a relatively soft, elastomeric material such as silicone so that the edges of the first mouth 33 and second mouth 41 can be momentarily enlarged to allow an object having a diameter equal to the maximum width diameter 31 of the first cavity 29 or the maximum width diameter 39 of the second cavity 37 to be pulled through the first and second mouths 33, 41, respectively, as indicated somewhat diagrammatically in FIG. 20.

The face surface 27 of the first body member 23 preferably has a groove 45 extending between the first and second cavities 29, 37 thereof for allowing an elongated length of thread, string, line, etc., such as a length of the bioresorbable line 15 of the bioresorbable string 11 of implantable beads, to be strung between the first and second cavities 29, 37 before the fluid mixture M has set. Thus, as shown in FIG. 7, the groove 45 may communicate with and extend between the depression 36 and the depression 44.

The first body member 23 preferably includes securement means for securing the line 15 strung across the first and second cavities 29, 37 to the first body member 23. The securement means preferably includes a slit or slot 47 cut into the first body member 23 and sized so as to frictionally grip the line 15, etc., when the line 15 is inserted into the slot 47. Thus, as clearly shown in FIG. 7, the slot 47 may communicate with the depression 36 opposite the groove 45.

A notch 49 is preferably provided in each end of the first body member 23 for reasons which will hereinafter become apparent. As shown in FIG. 7, each notch 49 may be located on one end of the body member 23, substantially midway between each side of the body member 23.

Figure 10:
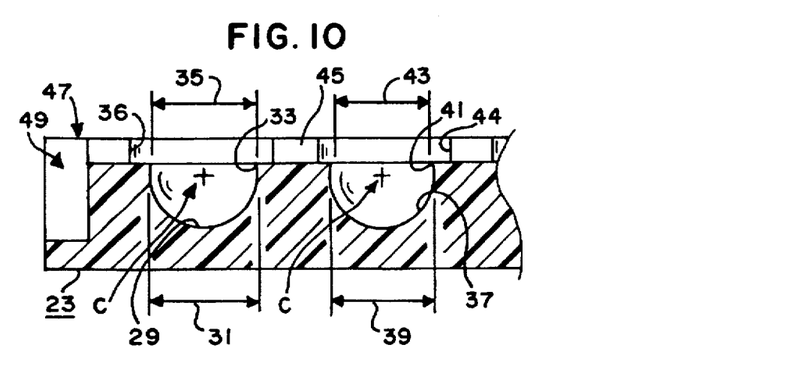
FIG. 10 is an enlarged sectional view of the first body member of the mold of FIG. 7.
Figure 11:
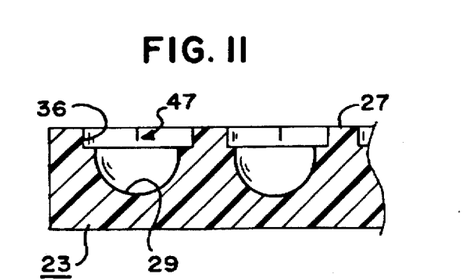
Figure 12:
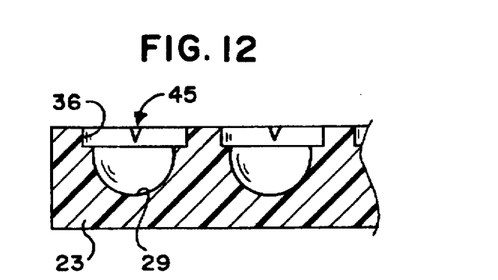
FIG. 12 is an enlarged sectional view similar to FIG. 11 but looking in the opposite direction.
Figure 13:
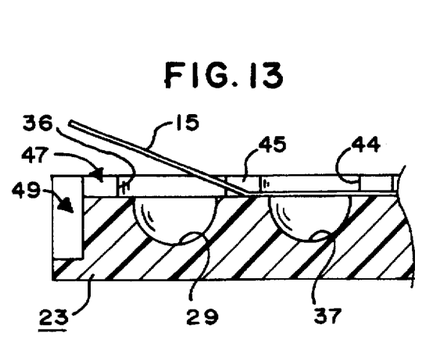
FIGS. 13-20 are somewhat diagrammatic sectional views of portions of the mold of FIG. 7, showing steps in the method of manufacturing a string of implantable beads using the mold of FIG. 7.

While the number and shape of cavities in the face surface 27 of the first body member 23 will depend on the desired number and shape of the beads to be molded thereby, to produce spherical beads such as the beads 13, each cavity 29, 37 preferably includes a contour having a semispherical shape with the geometric center C of each cavity 29, 37 (i.e., of the portion of the sphere defined by each cavity 29, 37) located a distance below the respective mouth 33, 41 as clearly shown in FIG. 10. The first body member 23 preferably has a multitude of cavities and associated mouths and enlarged counterbore-like depressions. For example, in the specific embodiment shown in FIG. 7, the first body member 23 has three identical rows of cavities and associated mouths and enlarged counterbore-like depressions with each row having ten cavities and associated mouths and enlarged counterbore-like depressions, thereby providing a total of thirty cavities and associated mouths and enlarged counterbore-like depressions, with each cavity joined to at least one adjacent cavity by a groove such as the groove 45 between the first and second cavities 29, 37, and with securing means such as the slot 47 extending from the cavity at each end of each row so that a length of line 15, etc., can be strung between all cavities of each row (providing, for example, a string of ten beads joined by a single line 15), and, if desired, between each row (providing, for example, a string of thirty beads joined by a single line 15), etc. By providing securing means at each end of each row, the length of line 15 extending down each row can be held tight.

The second body member 25 has a face or normally lower surface 51 for abutting or being positioned adjacent the face surface 27 of the first body member 23, and a back or normally upper surface 52.

Figure 17:
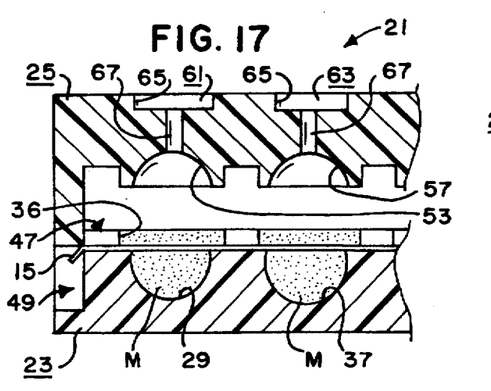

The second body member 25 preferably has a first cavity 53 in the face surface 51 thereof for coacting with the first cavity 29 and the first mouth 33 of the first body member 23 when the face surface 51 of the second body member 25 abuts or is positioned adjacent the face surface 27 of the first body member 23 to form a first combined cavity 55 as shown in FIG. 17.

Figure 18:
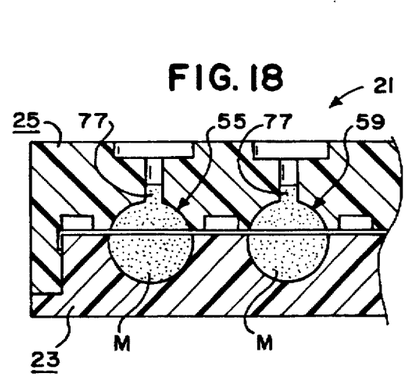
Figure 19:
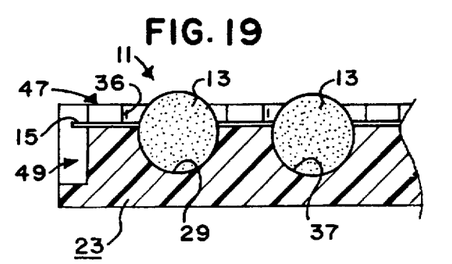

The second body member 25 preferably has a second cavity 57 in the face surface 51 thereof for coacting with the second cavity 37 and the second mouth 41 of the first body member 23 when the face surface 51 of the second body member 25 abuts or is positioned adjacent the face surface 27 of the first body member 23 to form a second combined cavity 59 as shown in FIG. 18.

The second body member 25 preferably has a first passageway means 61 extending between the first cavity 53 in the face surface 51 thereof and the back surface 52 thereof, etc., for allowing any excess quantity of the fluid mixture M to pass from the first combined cavity 55, and preferably has a second passageway means 63 extending between the second cavity 57 in the face surface 51 thereof and the back surface 52 thereof, etc., for allowing any excess quantity of the fluid mixture M to pass from the second combined cavity 59. Each passageway means 61, 63 preferably has a relatively large cavity or reservoir 65 preferably communicating with the back surface 52, and a relatively narrow corridor or passageway 67 extending from the respective cavity 53, 57 to the respective reservoir 65 for reasons which will hereinafter become apparent.

A tab 69 is preferably provided on each end of the second body member 25 for extending into and being guided by a respective notch 49 of the first body member 23 when the face surface 51 of the second body member 25 is brought into abutment or adjacent the face surface 27 of the first body member 23. As shown in FIGS. 7 and 8, each tab 69 may be located on one end of the body member 25, substantially midway between each side of the body member 25. Each tab 69 is preferably shaped to complement each respective notch 49 so that the tabs 69 and notches 49 coact to form guide means for causing the first and second cavities 53, 57 in the face surface 51 of the second body member 25 to align with the first and second mouths 33, 41, respectively, of the first body member 23 when the face surface 51 of the second body member 23 is caused to abut or positioned adjacent the face surface 51 of the second body member 25.

Figures 7, 8:
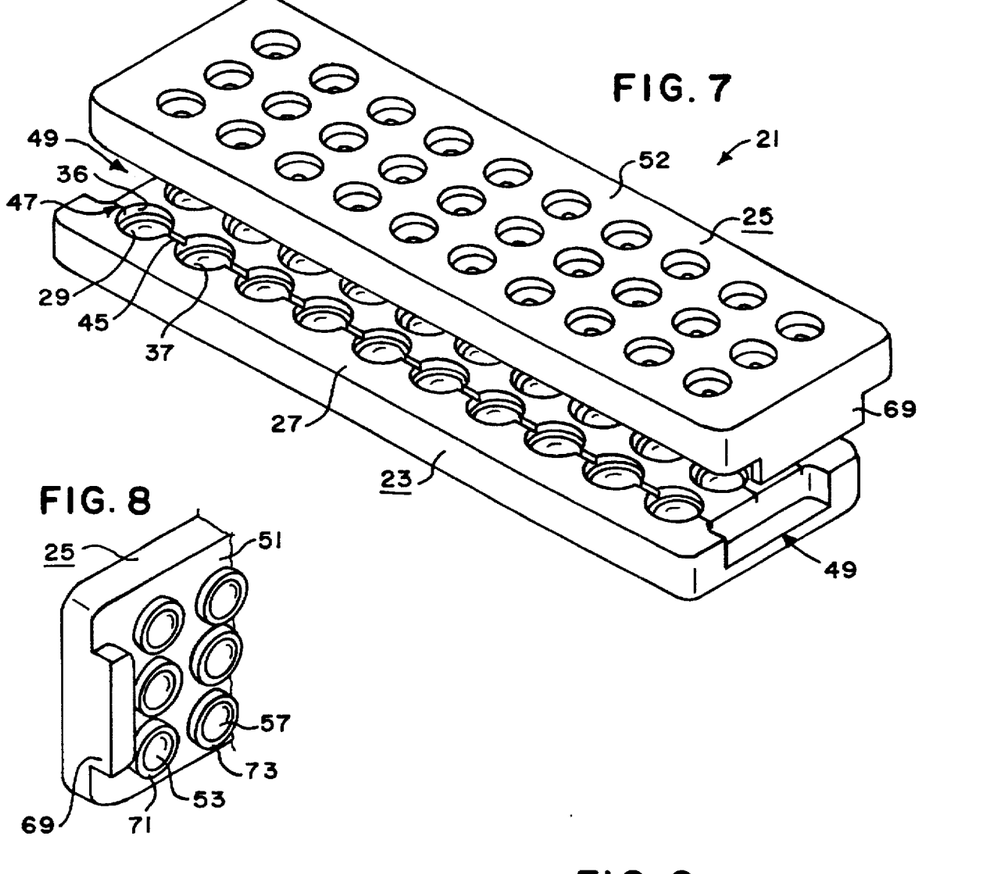
FIG. 7 is an exploded perspective view of first and second body members of the mold of the present invention for molding a string of implantable beads used to treat orthopedic tissue disorders.
FIG. 8 is a perspective view of a portion of the second body member of the mold of FIG. 7.
Figure 9:
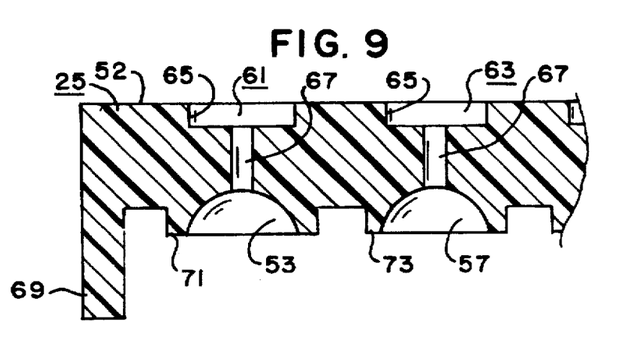
FIG. 9 is an enlarged sectional view of a portion of the second body member of the mold of FIG. 7.

The second body member 25 preferably includes a first boss member or piston 71 on the face surface 51 surrounding and contiguous with the first cavity 53 and a second boss member or piston 73 on the face surface 51 surrounding and contiguous with the second cavity 57 as clearly shown in FIGS. 8 and 9. Each boss member 71, 73 is preferably shaped and sized to complement the respective depression 36, 44 in the face surface 27 of the first body member 23 so that when the face surface 51 of the second body member 23 is caused to abut or positioned adjacent the face surface 51 of the second body member 25, each boss member 71, 73 will extend into the respective depression 36, 44 in a manner like a piston extending into a cylinder for reasons which will hereinafter become apparent.

While the number and shape of cavities in the face surface 51 of the second body member 25, etc., will depend on the desired number and shape of the beads to be molded thereby, the number and shape of cavities in the face surface 51 of the second body member 25 should be complementary to the number and shape of cavities in the face surface 27 of the first body member 23. Thus, to produce spherical beads such as the beads 13, each cavity 53, 57 preferably includes a contour having a shape that is less that a hemisphere so that each cavity 53, 57 will coact with each respective cavity 29, 37 of the first body member 23 to produce combined cavities 55, 59 having spherical contours. Likewise, the embodiment of the second body member 25 shown in the drawings preferably has three identical rows of cavities with each row having ten cavities, thereby providing a total of thirty cavities, etc.

The first and second body members 23, 25 may be constructed in various manners and out of various materials as will now be apparent to those skilled in the art. Preferably, the first and second body members 23, 25 are molded or otherwise constructed from an elastomeric material, preferably silicone, so that each body member 23, 25 is soft and elastic, and wherein at least a portion of the first body member 23 adjacent the first mouth 33 and the second mouth 41 is movable for allowing a string of beads to be easily removed therefrom as will hereinafter become apparent.

Figure 14:
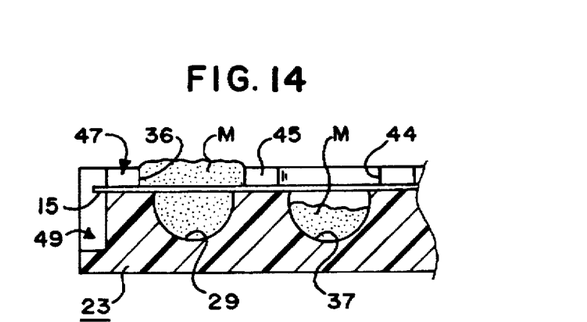
Figure 15:
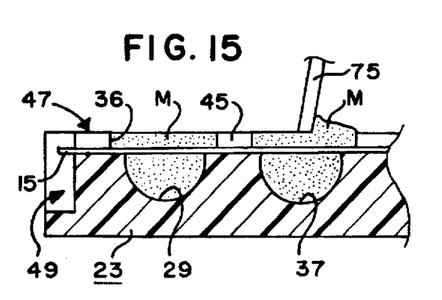
Figure 16:
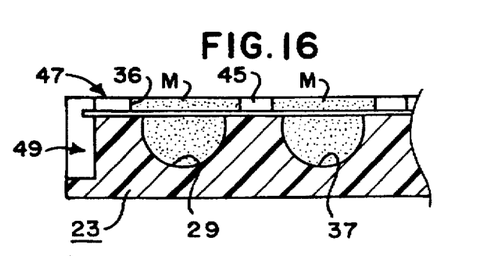
Figure 20:
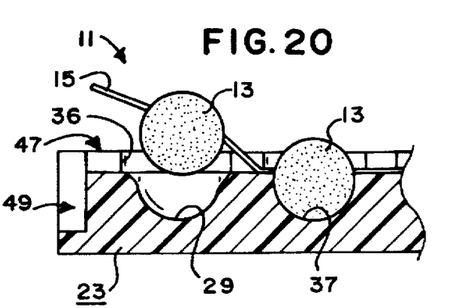

The method of manufacturing a string of implantable beads used to treat orthopedic tissue disorders of the present invention includes the step of providing a mold such as the mold 21. An elongated line such as the line 15 is strung between the number of cavities in the face surface 27 of the first body member 23 equal to the number of beads desired (e.g., if a string with two beads is desired, the line 15 is strung between the first and second cavities 29, 37 in the face surface 27 of the first body member 23) by merely stringing the line 15 across each of the desired cavities and into the grooves 45 extending between the desired cavities. The ends of the line 15 can be secured to the first body member 23 merely by pulling the opposite ends thereof tight and into the slots 47 so that the line 15 will be frictionally held to the body member 23. Next, the desired cavities in the body member are filled with a quantity of the fluid mixture M. For example, to fill the first and second cavities 29, 37 of the body member 23 with a fluid mixture M, a quantity of the fluid mixture M is merely inserted through the first and second mouths 33, 41 into the first and second cavities 29, 37, respectively, until the cavities 29, 37 and mouths 33, 41 are filled with the fluid mixture M as shown in FIGS. 14–16. A tool 75 such as a scraper having a flat blade or the like can pulled across the face surface 27 of the first body member 23 after the fluid mixture M has been inserted into the cavities as shown in FIG. 15 to even out and level the fluid mixture M in the cavities, etc. Next, the second body member 25 can be combined with the first body member 23 by merely inserting the tabs 69 into the respective notches 49 and moving the second body member 25 against the first body member 23 until the boss members 71, 73 extend into the respective depression 36, 44 similar to a piston extending into a cylinder, until the fluid mixture M in the depressions 36, 44 is forced into the respective cavity 53, 57 and the cavities 29, 37, 53, 57 coact to form the first and second combined cavities 55, 59, etc. The depressions 36, 44 are preferably sized so that the volume of each depression 36, 44 is at least equal to, and preferably slightly larger than, the volume of the respective cavity 53, 57 whereby the fluid mixture M in the depressions will completely fill the respective cavity 53, 57, and preferably extend into the respective passageway means 61, 63 to form a riser 77 as shown in FIG. 18. The first and second body members 23, 25 are then left combined until the fluid mixture M has had time to set. The length of time required for the fluid mixture M to set will vary depending on the specific composition of the fluid mixture M, etc. In any event, after sufficient time has past for the fluid mixture M to set and harden (e.g., after 15 minutes or so), the second body member 25 is removed from the first body member 23 by merely pulling the second body member 25 away from the first body member 23. Because of the specific design of the cavities 29, 37 in the first body member 23 (e.g., because the maximum width dimensions 31, 39 of the cavities 29, 37 are greater than the minimum width dimensions 35, 43 of the mouths 33, 41 and because the geometric centers C of the cavities 29, 37 are located a distance below the respective mouth 33, 41), the string 11 of beads will remain secured to the first body member 23 as the second body member 25 is removed from the first body member 23. However, once the second body member 25 has been removed from the first body member 23 and the string 11 of beads, the set string 11 of beads can be easily removed from the first body member 23 by merely pulling the line 15 away from the first body member 23 as shown in FIG. 20, causing each bead 13 to spread or move apart the movable portion of the respective mouth 33, 41 as that bead 13 is pulled out of the respective cavity 29, 37 (because the body members 23, 25 are preferably made of a soft, elastic material, the entire lip portion of each mouth 33, 41 is movable and will spread apart when a bead 13 is pulled therefrom).

Although the present invention has been described and illustrated with respect to preferred embodiments and preferred uses therefor, it is not to be so limited since modifications and changes can be made therein which are within the full intended scope of the invention.

We claim:

1. A bioresorbable string of implantable beads for implanting in a void to treat orthopedic tissue disorders, the bioresorbable string of implantable beads comprising:
   (a) a plurality of bioresorbable beads, each of the plurality of bioresorbable beads consisting essentially of calcium sulfate and a quantity of a drug suitable for treating tissue disorders; and
   (b) a bioresorbable line extending between and joining each of the plurality of bioresorbable beads.

2. The bioresorbable string of implantable beads of claim 1 in which the quantity of drug includes an antibiotic.

3. The bioresorbable string of implantable beads of claim 1 in which the quantity of drug includes an antineoplastic substance.

4. The bioresorbable string of implantable beads of claim 1 in which the quantity of drug includes an analgesic.

5. The bioresorbable string of implantable beads of claim 1 in which the bioresorbable line consists of a bioresorbable suture.

6. The bioresorbable string of implantable beads of claim 1 in which the shape of the plurality of bioresorbable beads is selected to provide an optimum rate of resorption and drug delivery.

* * * * *